United States Patent [19]

Hesse

[11] Patent Number: Plant 6,840

[45] Date of Patent: Jun. 6, 1989

[54] CHRYSANTHEMUM PLANT NAMED VENOY

[75] Inventor: Peter S. Hesse, Bradenton, Fla.

[73] Assignee: Ball Seed Company, W. Chicago, Ill.

[21] Appl. No.: 150,068

[22] Filed: Jan. 29, 1988

[51] Int. Cl.[4] ..... A01H 5/00

[52] U.S. Cl. ..... Plt./77

[58] Field of Search ..... Plt./77

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

A Chrysanthemum plant named Venoy having white, incurved decorative type ray florets, nine week response, freely branching and vigorous growth habits, an ability to be grown either as a disbud or CBR, good performance under high light conditions, and excellent flower substance and keeping quality.

2 Drawing Sheets

The present invention comprises a new and distinct cultivar of *Dendranthema grandiflora,* hereinafter referred to by the cultivar name Venoy.

Venoy is a product of a planned breeding program which had the objective of creating new Chrysanthemum cultivars having white decorative flowers, and freely branching and compact habits ideally suited for pot mum culture. Such traits in combination were not present or needed improvement in previously available commercial cultivars.

Venoy was originated from a hybridization made by applicant in a controlled breeding program in Parrish, Fla. in 1982. The female parent was Surf, disclosed in U.S. Plant Pat. No. 4,585. The male parent of Venoy was Paragon, disclosed in U.S. Plant Pat. No. 3,368. Venoy was discovered and selected as one flowering plant within the progeny of the stated parentage by Peter S. Hesse on Nov. 24, 1982 in a controlled environment in Parrish, Fla.

The first act of asexual reproduction of Venoy was accomplished when vegetative cuttings were taken from the initial selection in March, 1983 in a controlled environment in Parrish, Fla. by a technician working under formulations established and supervised by Peter S. Hesse. Horticultural examination of selected units initiated in November, 1983 has demonstrated that the combination of characteristics as herein disclosed for Venoy are firmly fixed and are retained through successive generations of asexual reproduction.

Venoy has not been observed under all possible environmental conditions. The phenotype may vary significantly with variations in the environment such as temperature, light intensity, and day length. The following observations, measurements and comparisons describe plants grown in Parrish, Fla. under greenhouse conditions which approximate those generally used in commercial practice.

The following traits have been repeatedly observed and are determined to be basic characteristics of Venoy, which in combination distinguish this Chrysanthemum as a new and distinct cultivar:

1. White decorative pot mum, with the ray florets being slightly incurved.
2. Produces a saleable pot when grown either as a disbud (all lateral buds removed, only the terminal bud remains) or CBR (center bud removal, lateral buds allowed to develop and flower).

3. Nine (9) week flower response.
4. Performs well year around under high light.
5. Freely branching and a vigorous growth habit.
6. Diameter of capitulum 10–12 cm when grown as a disbud.
7. Ray florets approximately 3–6 cm long and 1–2 cm wide.
8. Very few disc florets (less than 20) per capitulum.
9. Immature ray florets appear to be a pale yellow-green when viewed from a distance of 30 cm or more.
10. Excellent flower substance and keeping quality.

Of the many commercial cultivars known to the prsent inventor, the most similar in comparison to Venoy is its maternal parent Surf. In comparison to Surf, Venoy has a one week later flower response, better flower substance, more incurved flower form, and a more vigorous growth habit. The flower color and decorative type of Venoy are similar to those same characteristics of Surf.

The accompanying photographic drawings show typical inflorescence and foliage characteristics of Venoy, with colors being as nearly true as possible with illustrations of this type.

Sheet 1 is a black and white photograph of Venoy grown as a disbud with a few flowers being colored to show the yellow-green immature center florets.

Sheet 2 is a black and white photograph of Venoy, grown by removing the center bud and allowing the lateral buds to bloom, with a few flowers being colored to show the yellow-green immature center florets.

In the following description, color references are made to The Royal Horticultural Society Colour Chart. The color values were determined between 1:00 and 1:30 p.m. on Jan. 4, 1988 under fluorescent lighting at Parrish, Fla.

Classification:

*Botanical.*—*Dendranthema grandiflora,* cv. Venoy.

*Commercial.*—Decorative pot mum.

INFLORESCENCE

A. Capitulum:

*Form.*—Flat.

*Type.*—Double.

*Diameter across face.*—10–12 cm when grown as a disbud.

B. Corolla of ray florets:

*Color (general tonality from a distance of three meters).*—White.

*Color (upper and lower surfaces).*—155D.

C. Corolla of disc florets:

*Color (mature).*—Yellow.

*Color (immature).*—Yellow-green.

D. Reproductive organs:

*Androecium.*—Present in disc florets only.

*Gynoecium.*—Present in both disc and ray florets.

PLANT

A. General appearance:

*Height.*—30 cm above the edge of the pot. Height can vary depending upon growing conditions and growth regulator applications.

B. Foliage:

*Color (upper surface).*—147A.

*Color (lower surface).*—147B.

*Shape.*—Ovate, lobed with irregular tooth margins.

I claim:

1. A new and distinct cultivar of Chrysanthemum plant named Venoy, as illustrated and described, and parts thereof.

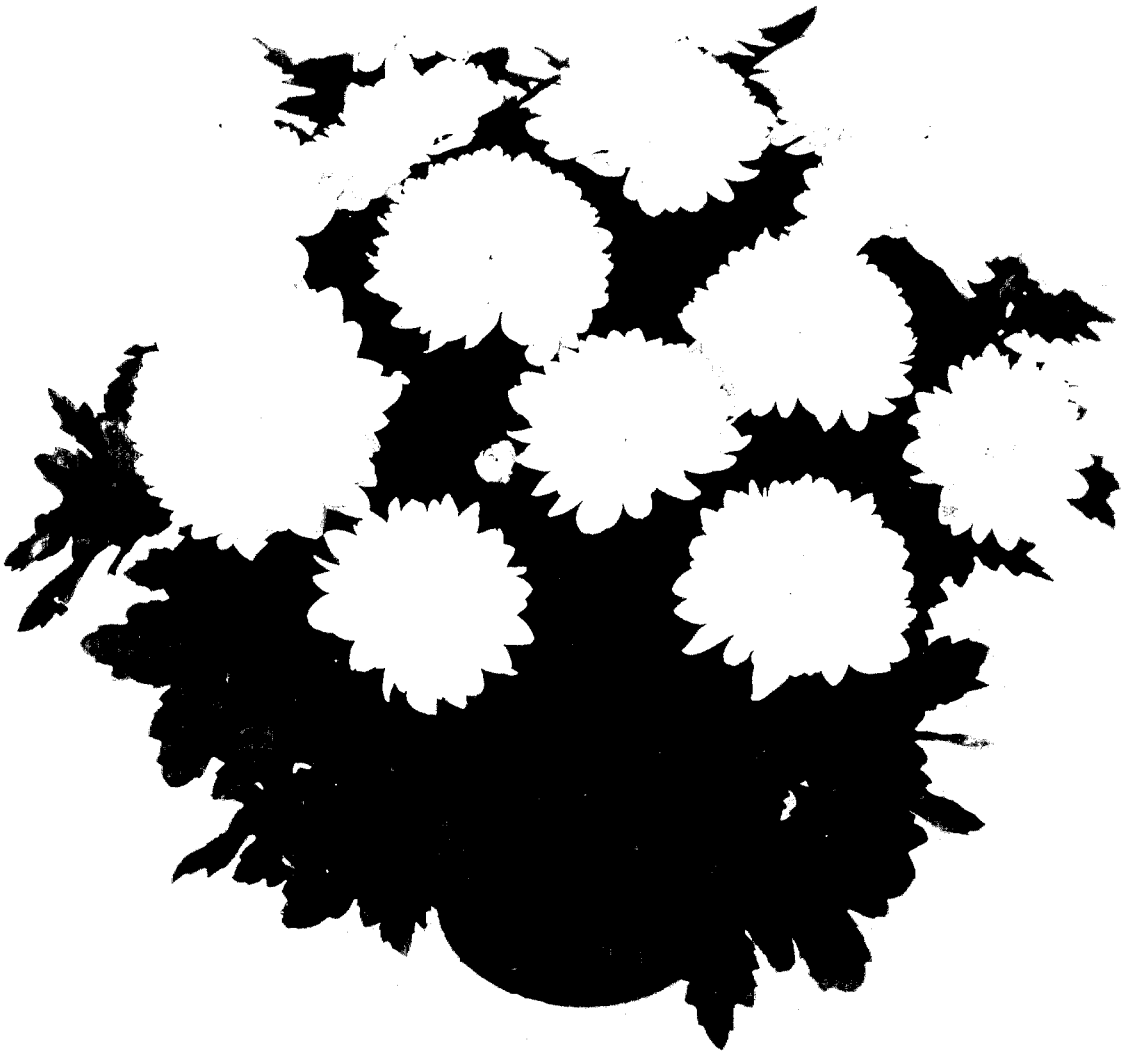

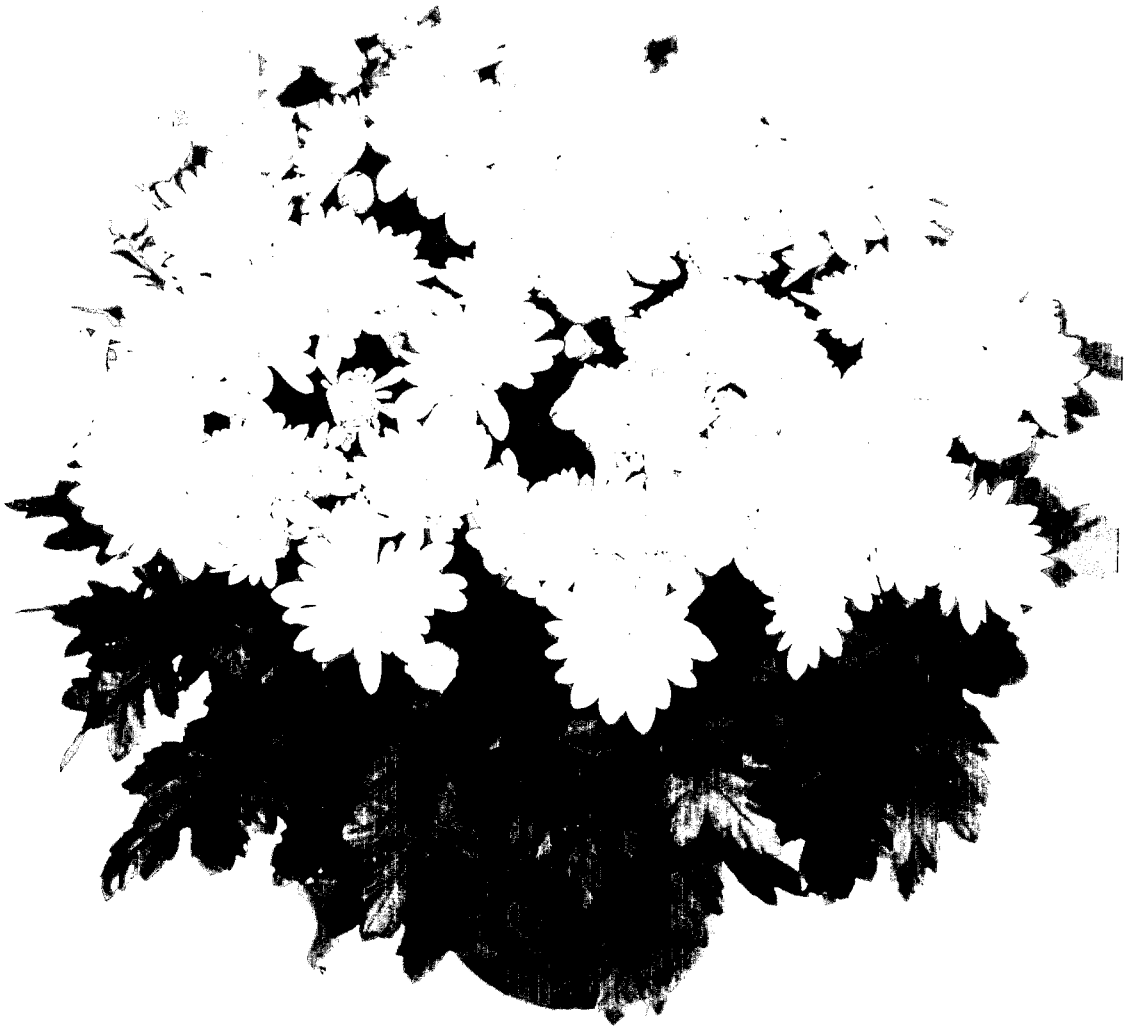

* * * * *